United States Patent [19]

Domb et al.

[11] Patent Number: 4,789,724

[45] Date of Patent: * Dec. 6, 1988

[54] PREPARATION OF ANHYDRIDE COPOLYMERS

[75] Inventors: Abraham J. Domb, Brookline; Robert S. Langer, Somerville, both of Mass.

[73] Assignee: Massachusetts Institute of Technology, Cambridge, Mass.

[*] Notice: The portion of the term of this patent subsequent to Jul. 12, 2005 has been disclaimed.

[21] Appl. No.: 920,724

[22] Filed: Oct. 17, 1986

[51] Int. Cl.$^4$ .............................................. C08G 67/04
[52] U.S. Cl. .................................. 528/176; 528/193; 528/194; 528/206; 528/271
[58] Field of Search ............... 528/176, 193, 194, 206, 528/271

[56] References Cited

U.S. PATENT DOCUMENTS

| 2,071,251 | 2/1937 | Carothers | 528/230 |
| 2,958,678 | 11/1960 | Conix | 528/86 |
| 2,960,493 | 11/1960 | Conix | 528/206 |
| 3,766,145 | 10/1973 | Thompson | 528/366 |
| 3,914,401 | 10/1975 | Sharabash | 424/462 |
| 3,960,150 | 6/1976 | Hussain et al. | 424/428 |

FOREIGN PATENT DOCUMENTS 840846 7/1960 United Kingdom .
968715 9/1964 United Kingdom .

OTHER PUBLICATIONS

John E. Bucher and W. Clifton Slade, The Anhydrides of Isophthalic and Terephthalic Acids, *J. Amer. Chem. Soc.* 32, 1319 (1909).
Naoya Yoda, Synthesis of Polyanhydrides. XI., *Makromol. Chem.* 36 (1962).
Naoya Yoda, Syntheses of Polyanhydrides, XII. Crystalline and High Melting Polyamidepolyanhydride of Methylenebis (p-Carboxyphenyl)amide, *Journal of Polymer Science:* Part A, vol. I, 1323 (1962).
Naoya Yoda, Synthesis of Polyanhydrides. II. New Aromatic Polyanhydrides with High Melting Points and Fiber-Forming Properties, *Makromol. Chem.* 32, 1 (1959).
Naoya Yoda, Synthesis of Polyanhydrides. X. Mixed Anhydrides of Aromatic and Five-Membered Heterocyclic Dibasic Acids, *Makromol. Chem.* 10 (1962).
Naoya Yoda and Akihisa Miyake, Synthesis of Polyanhydride. I. Mixed Anhydride of Aromatic and Aliphatic Dibasic Acids, *Makromol. Chem.* 32 (10), 1120 (1959).
Julian W. Hill and Wallace H. Carothers, Studies of Polymerization and Ring Formation. XIX. Many--Membered Cyclic Anhydrides, *J. Amer. Chem. Soc.* 55, 5023 (1933).
A Conix, Poly[1,3-Bis(p-Carboxyphenoxy)-Propane Anhydride], *Macromolecular Syntheses*, vol. two, 95 (1966).
Julian W. Hill and Wallace H. Carothers, Studies of Polymerization and Ring Formation. XIV. A Linear Superpolyanhydride and a Cyclic Dimeric Anhydride from Sebacic Acid, *J. Amer. Chem. Soc.* 54, 1969 (1932).
Polyanhydrides, *Ency. of Poly. Sci. & Tech.* 10, 630 (1969).

*Primary Examiner*—Harold D. Anderson
*Assistant Examiner*—Frederick Krass
*Attorney, Agent, or Firm*—Kilpatrick & Cody

[57] ABSTRACT

A method for preparation of very pure anhydride copolymers with high yield. The anhydride copolymers, consisting of aromatic and aliphatic diacids are formed by melt condensation of individually prepared, pure, isolated prepolymers. The method of preparation is characterized by high yield, reproducibility, polymer purity and controlled composition, and is a short and convenient procedure. The polyanhydrides produced by the disclosed method are particularly well suited to biomedical applications requiring low levels of toxic or inflammatory contaminants and physical and mechanical properties which closely conform to manufacturing specifications.

5 Claims, 2 Drawing Sheets

PREPARATION OF ANHYDRIDE COPOLYMERS

The United States Government has rights in this invention by virtue of National Institute of Health Grant No. 98000.

BACKGROUND OF THE INVENTION

The present invention is in the area of organic synthesis and, in particular, methods of synthesizing high purity anhydride copolymers.

Aromatic polyanhydrides were first synthesized in 1909 by Bucher and Slade, as reported in *J. Am. Chem. Soc.* 31, 1319 (1909). Aliphatic polyanhydrides were first prepared in 1932 by Hill and Carothers, as described in *J. Am. Chem. Soc.* 54, 1569 (1932) and 55, 5023 (1933). A number of aromatic and heterocyclic polyanhydrides, intended as substitutes for polyesters in textile applications, were further investigated over the next thirty years.

Only a few papers have been published on the preparation of anhydride copolymers. In these studies anhydride copolymers were produced by mixing a calculated amount of two diacids, e.g., aromatic and aliphatic diacids, and treating with acetic anhydride to yield the mixed prepolymer. The mixed prepolymer was then polymerized by heating under vacuum. The reaction is shown in equation 1. The mixed prepolymer was not isolated nor purified prior to polymerization.

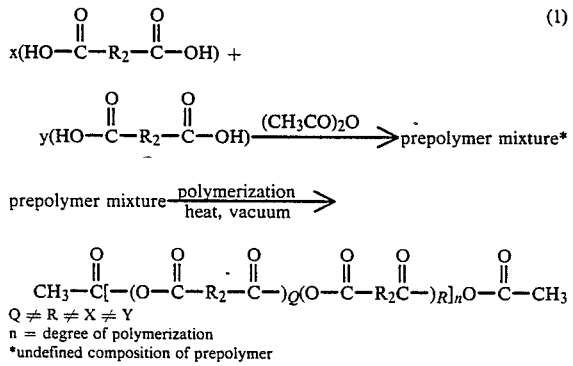

$Q \neq R \neq X \neq Y$
n = degree of polymerization
*undefined composition of prepolymer Using this method of preparation, N. Yoda et al. prepared anhydride copolymers composed of terephthalic acid, sebacic acid, adipic acid and five membered heterocyclic diacids, as described in *Makromol. Chem.* 56, 32 (1962), and *Bull. Chem. Soc. Japan* 1120 (1959) 32, Another anhydride copolymer composed of methylene bis(p-carboxyphenyl)amide and adipic acid was reported by N. Yoda in *Chem. High Polymers Japan* 19, 613 (1962). Unpurified mixed prepolymers were used in all these studies.

In a recent study by Leong et al., reported in *J. Biomed Mat. Res.*, 19, 941 (1985), anhydride copolymers composed of bis(p-carboxyphenoxy)propane and sebacic acid were prepared. The copolymers were prepared from the mixed prepolymers obtained when the calculated amount of CPP and sebacic acid were treated with acetic anhydride. The mixed prepolymer was isolated after several weeks of crystallization at $-20°$ C. The composition of the final polymer was not controlled. Polymerization of the mixed prepolymers yielded polymers with molecular weights of 12,030. Unsuccessful attempts were made to obtain the copolymers by polycondensing the mixture of individually prepared prepolymers, especially sebacic acid prepolymers.

It is therefore an object of the present invention to provide a method for preparation of highly pure anhydride copolymers having a controlled composition, especially for use in biomedical applications.

It is a further object of the present invention to provide a method for preparation of highly pure anhydride copolymers with controlled composition which is reproducible, has a high yield and is quick.

It is a still further object of the present invention to provide a method for preparation of highly pure anhydride copolymers wherein prepolymers of the diacids are produced which can be combined to yield a wide variety of copolymers having an actual composition which is close to the calculated composition.

It is another object of the invention to provide a method for preparation of highly pure anhydride copolymers for use in preparing high molecular weight polyanhydrides.

SUMMARY OF THE INVENTION

The invention is a method of synthesis of highly pure anhydride copolymers of known composition wherein the key element is the use of individually prepared, pure prepolymers. Calculated amounts of the individual prepolymers, e.g. aromatic and alphatic prepolymers, are mixed together and polymerized to form copolymers. High molecular weight polyanhydrides are produced by polymerization of the prepolymers at a temperature between 150° C. and 220° C. for 10 to 240 minutes, preferably 180° C. for 90 minutes, under high vacuum.

Examples of anhydride copolymers composed of the following diacids: sebacic acid (SA), bis(p-carboxyphenoxy)propane (CPP), adipic acid, bis(p-carboxyphenoxy)hexane (CPH), isophthalic acid (Isoph.) 1,4 phenylene dipropionic acid and dodecanedioic acid (DD), are polymerized from pure isolated prepolymers by a melt polycondensation process.

Polyanhydrides prepared from the very pure, isolated prepolymers are especially useful for biomedical applications because of the agreement between calculated and actual composition, reproducible molecular weights and degradation kinetics, lack of inflammatory or toxic contaminants, and mechanical properties such as film formation. Higher molecular weights can be generated by the addition of coordination catalysts to the copolymer mixture.

DETAILED DESCRIPTION OF THE INVENTION

Figure 1:
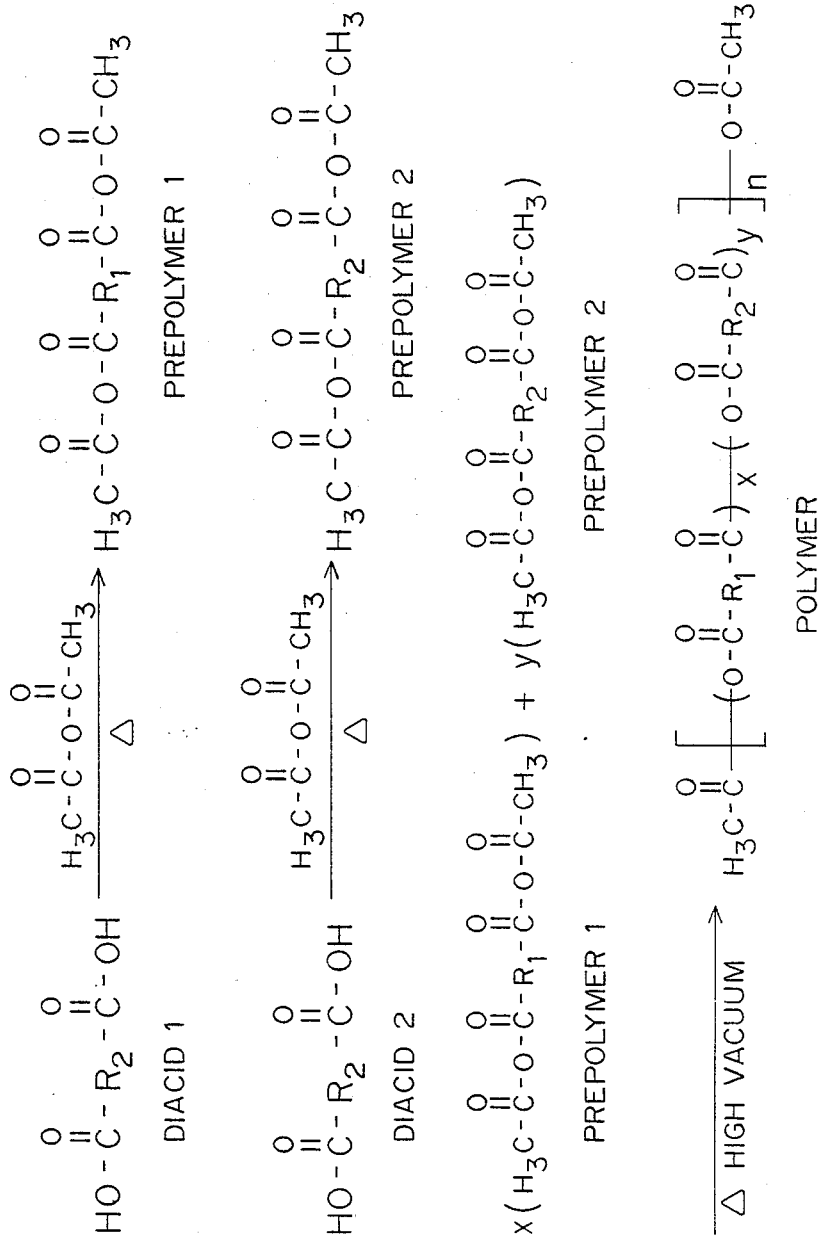
FIG. 1 is the synthesis of a pure anhydride copolymer according to the present invention.
Figure 2:
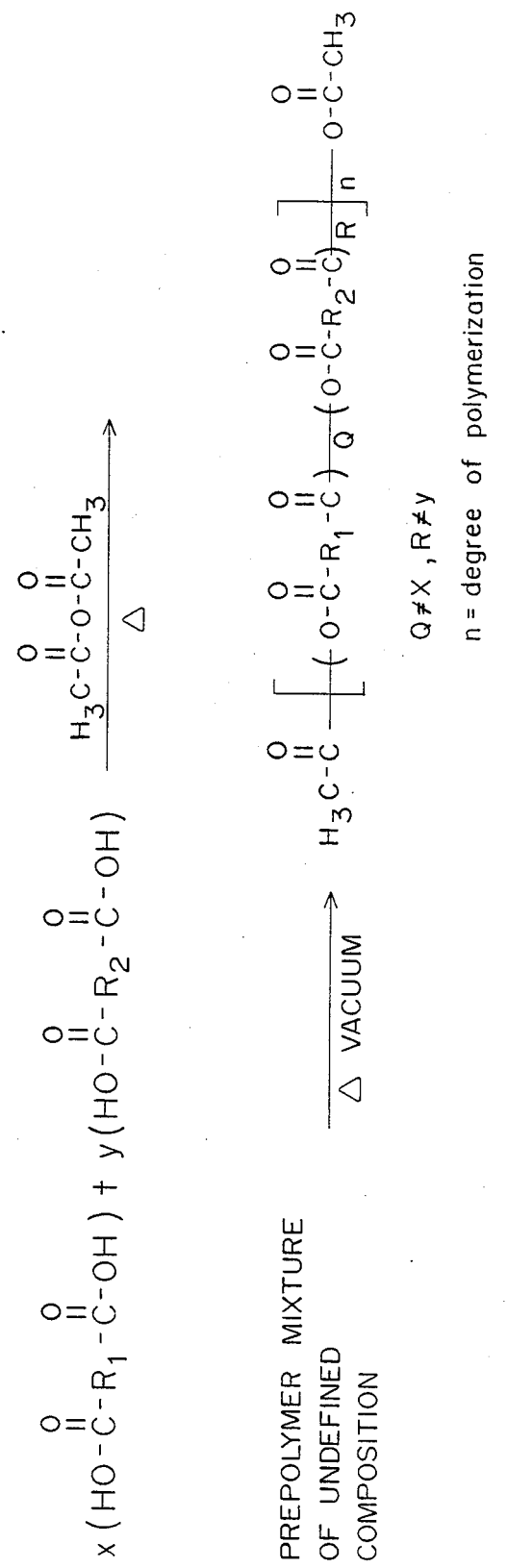
FIG. 2 is the synthesis of ananhydride copolymer according to the prior art.

Anhydride copolymers are synthesized by melt condensation from a mixture of individually synthesized and purified mixed anhydride prepolymers prepared by heating diacids and acetic anhydride as shown in FIG. 1. The prior art method of synthesis is shown in FIG. 2 wherein the diacids are first mixed together, then refluxed with acetic anhydride to form the prepolymers.

The method according to the present invention is used in the following non-limiting examples to synthesize anhydride prepolymers which can then be combined and polymerized to form anhydride copolymers with controlled composition. Individually prepared, pure, isolated prepolymers are made and purified within two work days with 50 to 80% yield. Calculated amounts of the prepolymers, such as CPP prepolymers and sebacic acid prepolymers, are then mixed together and polymerized, for example, at 180° C. for 90 minutes under high vacuum.

The prepolymer data analysis is summarized in Table 1. The data for the copolymers prepared from these prepolymers is summarized in Table 2. High molecular weight anhydride copolymers with high reproducibility in polymer composition and molecular weight are obtained.

TABLE 1

Characterization of Prepolymers

| Prepolymer of: | Mp | GPC Analysis | | | NMR Analysis[b] | |
| --- | --- | --- | --- | --- | --- | --- |
| | | Mw | Mn | Dp[a] | Dp | IR[c] |
| Sebacic acid | 67–69 | 1620 | 825 | 3.9 | 5 (2.22:1.32)[d] | 1810,1740 |
| Dodecanedioic acid | 76–77 | 2410 | 1250 | 4.7 | 9 (2.22:1.27)[d] | 1810,1740 |
| Adipic acid | 62–63 | 1765 | 694 | 4.0 | 6 (2.23:1.74)[d] | 1810,1740 |
| 1,4 Phenylene dipropionic acid | 74–75 | 1985 | 915 | 4.0 | 5 (2.18:7.11)[d] | 1800,1735 |
| Bis(p-Carboxyphenoxy) propane | 104–106 | 495 | 484 | 1.3 | 1.4 (2.30:7.1–8.1)[d] | 1800,1730 |
| Bis(p-Carboxyphenoxy) hexane | 92–94 | 573 | 490 | 1.1 | 1.3 (2.30:7.1–8.1)[d] | 1800,1735 |
| Isophthalic acid | 56–58 | 484 | 376 | 1.9 | 1.6 (2.43:7.4–8.6)[d] | 1800,1735 |

[a]Dp based on the Mn of the GPC analysis.
[b]Determined from 'H—NMR analysis.
[c]Characteristic for anhydride bonds.
[d]Chemical shift in PPM of the methyl terminal and the representative peak of the repeating unit.

TABLE 2

Characterization of Anyhdride Copolymers

| | % Aliphatic Units | | |
| --- | --- | --- | --- |
| | (calculated) | (found) | |
| CPP:SA | 80 | 80 ± 2 | 115,000 ± 5,000 |
| | 70 | 70 ± 2 | 78,000 ± 4,500 |
| | 50 | 50 ± 2 | 32,000 ± 3,000 |
| Isoph:SA | 80 | 81 ± 2 | 112,000 ± 5,400 |
| | 50 | 49 ± 1 | 30,000 ± 2,900 |
| CPP:DD | 80 | 79 ± 2 | 122,000 ± 6,100 |
| | 50 | 50 ± 2 | 31,000 ± 3,200 |
| CPH SA | 80 | 79 ± 2 | 76,400 ± 6,800 |
| CPH:DD | 80 | 80 ± 2 | 84,900 ± 5,600 |
| | 50 | 51 ± 1 | 36,550 ± 3,420 |
| CPP:adipic acid | 80 | 82 ± 2 | 56,800 ± 3,800 |

Copolymers prepared from individually prepared prepolymers in Table 1 were polymerized at 180° C. for 90 min. Results are an average of five separate polymerizations.

The following materials and methods were used in the examples:

Chemicals: Sebacic acid, dodecannedioic acid and adipic acid (99%, Aldrich Chemical Co., Milwaukee, Wis.) were recrystallized three times from ethanol and 1,4 phenylene dipropionaic acid (98%, Aldrich Chemical Co.) was recrystallized from acetone before use. Bis(p-carobxyphenoxy)alkanes were synthesized according to the method described by A. Conix in *Marcomol. Synth.* 2, 95 (1966) and cleaned by extraction with acetone and ether before use. Isophthalic acid (99%, Aldrich Chemical Co.) was recrystallized from ethanol. All solvents were analytical grade.

Instrumentation: Infared spectroscopy was performed on a Perkin-Elmer Spectrophotometer Model 1430. Polymeric samples were film cast onto NaCl plates from solutions of the polymer in chloroform. Prepolymer samples were either pressed into KBr pellets or dispersed in nujol onto NaCl plates.

Thermal analysis of polymers was performed on a Perkin Elmer DSC-2 differential Scanning Calorimeter employing a heating rate of 20° C./min. The melting point of prepolymers was determined on a Fisher Johns melting point apparatus. The molecular weights of the polymers and prepolymers were estimated on a Perkin Elmer GPC system consisting of a series 10 pump, a 3600 Data Station with an LKB 214 - rapid spectral detector at 254 nm wavelength. Samples were eluted in chloroform through two Pl Gel columns (Polymer Laboratories; 100 Angstroms and 1000 Angstroms pore sizes) in series at a flow rate of 1.5 ml/min. Polystyrene (Polyscience) was used as the calibration standard. Viscosity of polymers was measured in an Ubbelohde Viscometer (cannon 75) at 23° C. using 1, 0.5 and 0.25% w/v polymer in chloroform solution. 'H-NMR spectra were run on a Bruker AM-250 spectrometer in $CHCl_3$.

Determination of Prepolymer and Polymer Composition

The composition of anhydride copolymers is determined by 'H-NMR from the ratio of the peaks integration of the copolymer units, for example, the composition of CPP:SA copolymers is determined by 'H-NMR from the ratio of the peaks integration at 1.3 PPM (8H, Sebacic acid) and 6.9–8.2 PPM (8H, CPP).

General Method for Polymer Synthesis

Polyanhydrides are synthesized by melt polycondensation of mixed anhydrides of diacids and acetic anhydride. Aliphatic mixed anhydride prepolymers are prepared by refluxing the dicarboxylic acid monomers (40 g) in acetic anhydride (200 ml) for 20 to 90 minutes. The excess acetic anhydride is removed to dryness under vacuum at 60° C. The crude prepolymer is recrystallized from dry toluene. The crystals are then immersed in a 1:1 mixture of dry petroleum ether and ethyl ether overnight to extract traces of acetic anhydride and toluene. The pure crystals are dried under vacuum over calcium chloride (75–88% yield). Aromatic monomers are refluxed for 15 to 30 minutes, then the unreacted diacid (5 to 10%) removed by filtration. The solution is concentrated to 150 ml and allowed to crystallize overnight at 0° C. The crystals are then immersed in dry ether (200 ml) overnight with stirring to extract traces of acetic anhydride.

The purified prepolymer is washed with dry ether and dried under vacuum over calcium chloride (42–50% yield). The prepolymers are characterized by GPC, 'H-NMR and IR analysis.

The amounts of prepolymers (as calculated below) then undergo melt polycondensation as follows: In a typical reaction, CPP prepolymer is mixed with sebacic acid prepolymer in a glass tube (2×20 cm) with a side arm equipped with a capillary nitrogen inlet. The tube is immersed in an oil bath at 180° C. After the prepolymers are melted, approximately 1 minute, high vacuum (10–4 mm Hg) is applied through the side arm. The condensation product, acetic anhydride, is collected in an acetone/dry ice trap. During the polymerization, a strong nitrogen sweep with vigorous agitation of the melt is performed for 30 seconds every 15 minutes. The crude polymer is purified by precipitation in dry petroleum ether from a dichloromethane solution. The precipitate is then extracted with anhydrous ether for several hours at room temperature.

Calculations

The calculated amounts of prepolymers to be mixed for the synthesis of an x:y copolymer, where x:y is the molar ratio of copolymer units, is as follows:

$$x\left(\frac{Mn_1}{Dp_1}\right) + y\left(\frac{Mn_2}{Dp_2}\right)$$

grams of prepolymer 1    grams of prepolymer 2 wherein x and y are the molar ratios of prepolymers 1 and 2 in the copolymer,
Mn is the number average molecular weight of the prepolymer as determined by GPC, and
Dp is the number of units in the prepolymer as calculated from:

$$Dp = \frac{Mn - 102}{Ru}$$

where 102 is the molecular weight of prepolymer end groups:

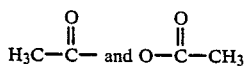

and Ru is the molecular weight of the repeating unit in the prepolymer.
For example:
for sebacic acid, the repeating unit is:

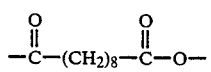

Ru=184 and
for CPP, the repeating unit is:

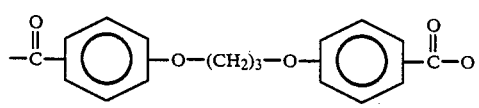

and Ru=308

Example of the preparation of 1,3 bis(p-carboxyphenoxy) propane:sebacic acid polymers (CPP:SA)

1. Preparation of pure, isolated CPP prepolymers.

A solution of 138 g (1.0 mole) of p-hydroxy benzoic acid and 80 g (2.0 moles) of sodium hydroxide in 400 ml of water is placed in a one liter three-necked flask equipped with a mechanical stirrer, a condenser, and a dropping funnel. 102 g (0.5 mole) of 1,3-dibromopropane is added through the funnel over a period of one hour, while the contents of the flask are stirred and kept at reflux temperature. The reaction mixture is refluxed for 3.5 hours after the addition of the 1,3-dibromopropane. 20 g (0.5 mole) of solid hydroxide is then added to the mixture, and the mixture refluxed for an additional two hours. Heating is then discontinued and the reaction mixture left standing overnight. The fine, powdery, white precipitate of the disodium salt is isolated by filtration and washed with 200 ml of methanol. The still wet precipitate is dissolved in one liter of distilled water with gentle heating.

The solution is extracted with 200 ml of ether to remove traces of dibromide, acidified with 6N sulfuric acid to a pH less than 2, the diacid isolated by filtration, and the diacid dried for 3 days in a lyophilizer. The yield is 120 g (76%).

40 g of CPP powder is then added to 500 ml boiling acetic anhydride (135° C.) under dry $N_2$. Reflux is stopped at 25 min and the solution filtered through a filter paper into another one liter round bottom flask. About 10% of the unreacted CPP is separated. The solution is concentrated to 150 ml by evaporation (evaporator with $CaCl_2$ trap). The solution is left at 0° C. to crystallize overnight. The crystals are separated by filtration and transferred to 200 ml of anhydrous diethyl ether in an Erlenmayer flask and allowed to swirl for several hours at room temperature. The white crystals are separated by filtration and dried in a $CaCl_2$ desiccator under vacuum. The CPP prepolymer is recovered with a yield of 50–60% and has a melting point of 104°–106° C. and IR-1810, 1740cm$^{-1}$.

2. Preparation of pure, isolated SA prepolymers.

30 g of sebacic acid are added to a 120 ml refluxing solution of acetic anhydride under $N_2$. Reflux is continued for 90 min. Sebacic acid is completely dissolved within 5 min. of reaction. Excess acetic anhydride is evaporated by an evaporator at 60° C. The oily material is left at room temperature to solidify. The solid is dissolved in 15 ml toluene with warming and the solution allowed to crystallize overnight at 0° C. The crystals are separated by filtration and transferred to 200 ml diethyl ether and petroleum ether 1:1 mixture, with stirring for 5 hours. The white crystals are separated by filtration and dried in a $CaCl_2$ desiccator under vacuum. The sebacic acid has a melting point of 64°–65° C. and IR-1810, 1740 cm$^{-1}$.

3. Polymerization of a CPP prepolymer:SA (20:80) prepolymer mixture.

CPP prepolymer (0.80 g, 2.0 mmole) is mixed with sebacic acid prepolymer (1.64 g, 8.0 mmole) in a glass tube (2×20 cm) (Kimax) with a side arm equipped with a capillary nitrogen inlet. The tube is immersed in an oil bath at 180+1° C. After the prepolymers are melted, approximately 1 min, high vacuum (less than 10$^{-2}$ mm Hg) is applied through the side arm. The condensation product, acetic anhydride, is collected in an acetone/dry ice trap. During the polymerization, a strong nitrogen sweep with vigorous agitation of the melt is performed for 30 seconds every 15 minutes. After 90 minutes, the polymer is removed under nitrogen to a dry glass vial. The crude polymer is ground to small particles using a micromill at low temp. ($H_2O$/ice cooling). The yield in this example is greater than 90%.

4. Purification of the CPP:SA (20:80) polymer.

The crude polymer is purified by precipitation in dry petroleum ether from dichloromethane solution as follows: 20 g of crude polymer is dissolved in 100 ml dichloromethane (analytical grade) at room temp. with magnetic stirring for about 20 min. The solution is pressure filtered through a 2 micron filter and dripped into 600 ml of dry petroleum ether (analytical grade) stirred with mechanical stirrer. A white fiber-like precipitate is obtained. After filtration, the precipitate is extracted with anhydrous ether (200 ml) for several hours at room temp. The ether is decanted out and the ether residue is removed by anhydrous evaporator under high vacuum (oil pump). The CPP:SA polymer has a melting point of 68°–70° C., molecular weight: $M_w$ (weight average molecular weight)=118,000, Mn=22,400 (by GPC analysis), composition of CPP:SA (21:79) (by 'H-NMR), and intrinsic viscosity of [n]=0.92 dl/g (chloroform, 23° C).

5. Polymerization of a CPP:SA (50:50) copolymer.

CPP prepolymer (2.0 g, 5 mmole) is mixed with sebacic acid prepolymer (1.15 g, 5 mmole) and polymerized at 180° C. under high vacuum (10 mm Hg) for 90 min using the same method as above. The CPP:SA (50:50) polymer has a melting point of 152° C., molecular weight: $M_w$=38,200, $M_n$=17,900 (by GPC analysis), intrinsic viscosity of [n]=dl/g (chloroform 23° C.), and composition of CPP:SA (50:50) (by 'H-NMR).

Examples of the preparation of 1,3 bis(p-carhoxyphenoxy) propane: dodecanedioic acid polymers (CPP:DD)

1. Preparation of pure, isolated CPP prepolymer is as previously described.

2. Preparation of dodecanedioic acid prepolymer.

50 g of dodecanedioic acid are added to 250 ml boiling acetic anhydride under dry argon. Reflux is continued for 60 minutes. Excess acetic anhydride is removed by an evaporator at 60° C. to yield a white solid. The solid is dissolved in 20 ml dry toluene with gentle warming and the solution is allowed to crystallize overnight at 0° C. The crystals are separated by filtration and extracted with 200 ml methyl ether and petroleum ether 1:1 mixture for 5 hours at room temperature. The pure crystals were dried under vacuum over calcium chloride to yield 47 g prepolymer with a melting point of 76° C. and IR-1810, 1740 cm-1.

3. Preparation of CPP:DD (20:80) copolymers.

CPP prepolymer (0.8 g, 2.0 mmole) is mixed with dodecanedioic acid prepolymer (2.0 g, 8.0 mmole) and polymerized at 180° for 90 min under high vacuum (less than $10^{-2}$ mm Hg). The polymer is purified as previously described. The polymer has a melting point of 75°–76° C., molecular weight: Mw =125,900, Mn =26,850 (by GPC analysis); a composition of CPP:DD (20:80) (by 'H-NMR) and intrinsic viscosity of [n]=1.16 dl/g (chloroform, 23° C).

4. Polymerization of CPP:DD (50:50) copolymer.

CPP prepolymer (1.6 g, 4.0 mmole) is mixed with DD prepolymer (1.0 g, 4.0 mmole) and polymerized at 180° C. for 90 min under high vacuum ($10^{-2}$ mm Hg). The polymer is purified as described in the first example. The polymer has a melting point of 158°–160° C., molecular weight: Mw =44,800, Mn =16,850, composition of CPP:DD (51:49) (by 'H-NMR), and intrinsic viscosity of [n]=0.76 dl/g.

5. Polymerization of CPP:DD (65:35) copolymer.

CPP prepolymer (2.6 g, 6.5 mmole) is mixed with DD prepolymer (0.88 g, 3.5 mmole) and polymerized at 180° C. for 90 min under high vacuum (less than $10^{-2}$ mm Hg). The polymer is purified as previously described. The polymer has a melting point of 194 to 195° C., molecular weight: Mw =32,000, Mn =10,100, composition of CPP:DD (64:36), and intrinsic viscosity of [n]=0.64 dl/g.

Example of the preparation of phenylene dipropionic acid copolymer with sebacic acid and 1,3 bis(P-carboxyphenoyl)propane 1. Sebacic acid and CPP prepolymers are prepared as previously described.

2. Preparation of phenylene dipropionic acid prepolymer.

60 g of PDP (phenylene dipropionic acid ) are added to 500 ml boiling acetic anhydride under dry argon. Reflux is continued for 60 minutes. Excess acetic anhydride is removed by an evaporator at 60° C. to yield a white solid. The solid is recrystallized from 30 ml toluene at 0° C. overnight. The crystals are then extracted with 200 ml of a diethyl ether and petroleum ether (1:1) mixture for 5 hours at room temperature. The pure crystals are dried under vacuum over calcium chloride to yield 61 g prepolymer with a melting point of 74°–75° C. and IR-1800, 1735 cm$^{-1}$.

3. Polymerization of PDP:SA (20:80) copolymer.

PDP prepolymer (0.91 g, 4 mmole) is mixed with SA prepolymer (3.28 g, 16 mmole) and polymerized at 180° C. under high vacuum (less than $10^{-2}$ mm Hg) for 90 min. The polymer is purified as previously described. The polymer has a melting point of 56°–59° C., molecular weight: Mw =84,920, Mn =15,650, intrinsic viscosity of [n]=0.68 dl/g, and composition of PDP:SA (20:80) (by 'H-NMR).

4. Preparation of PDP:SA (50:50) copolymer.

PDP prepolymer (1.14 g, 5 mmole) is mixed with SA prepolymer (1.0 g, 5 mmole) and polymerized at 180° under high vacuum (less than $10^{-2}$ mm Hg) for 90 min. The polymer is purified as previously described. The polymer has a melting point of 75°–77° C., molecular weight: Mw =58,900, Mn =12,400, intrinsic viscosity of [n]=0.64 dl/g, and composition of PDP:SA (49:51) (by 'H-NMR).

5. Preparation of PDP:CPP (50:50) copolymer.

PDP prepolymer (1.14 g, 5 mmole) is mixed with CPP prepolymer (2.0 g, 5 mmole) and polymerized at 180° under high vacuum (less than $10^{-2}$ mm Hg) for 90 min. The polymer is purified as previously described. The polymer has a melting point of 158°–160° C., molecular weight: Mw=34,400, Mn =10,100, intrinsic viscosity of [n]=0.65 dl/g, and composition of PDP:CPP (48:52) (by 'H-NMR).

6. Preparation of CPP:PDP:SA (50:25:25) copolymer.

CPP Prepolymer (2.0 g, 5 mmole) is mixed with PDP prepolymer (0.57 g, 2.5 mmole) and SA prepolymer (0.5 g, 2.5 mmole) and polymerized at 180° under high vacuum (less than $10^{-2}$ mm Hg) for 90 min. The polymer is purified as previously described. The polymer has a melting point of 142°–144° C., molecular weight: Mw =28,900, Mn =12,400, intrinsic viscosity of [n]=0.58 dl/g, and composition of CPP:PDP:SA (48:27:25) (by 'H-NMR).

Preparation of mixed prepolymer by the prior method (FIG. 2)

The yield and reproducibility of the anhydride copolymers produced by the prior art method were compared with the yield and reproducibility of anhydride copolymers produced by the method of the present invention as follows.

A calculated amount of the diacids (total of 50 g) was refluxed in acetic anhydride (500 ml) for 20 min. Unreacted material was removed by filtration, and the solution concentrated to 100 ml by vacuum evaporation. The solution was then left at $-20°$ C. for 3 weeks to crystallize. The yield and composition of the precipitate for mixed prepolymers of CPP:SA (20:80), CPP:SA (50:50), isoph:SA (20:80), and isoph:SA (50:50) are summarized in table 3.

In a typical reaction, 10.0 g (0.0316 mole) of CPP were mixed with 25.6 g (0.126 mole) sebacic acid and refluxed in 500 ml acetic anhydride for 30 min. The unreacted material (0.6 g, identified as CPP) is removed by filtration and the solution concentrated to 100 ml by vacuum evaporation. The solution is allowed to crystallize for 3 weeks at $-20°$ C. The precipitate is separated by filtration and washed with anhydrous ether (100 ml) to yield 14.8 g of mixed prepolymers with a composition of CPP:SA in a ratio of 35:65 (calculated 20:80), as determined by H-NMR, IR-1800, 1740 $cm^{-1}$.

TABLE 3

Characterization of mixed prepolymers

| Prepolymer composition* | (%) aliphatic monomer | | yield (%) |
|---|---|---|---|
| | calculated | found | |
| CPP:SA (20:80) | 80 | 65 | 15 |
| | 80 | 50 | 21 |
| | 80 | 72 | 25 |
| CPP SA (50:50) | 50 | 30 | 25 |
| | 50 | 45 | 34 |
| | 50 | 32 | 24 |
| Isoph:SA (20:80) | 80 | 72 | 25 |
| | 80 | 65 | 33 |
| | 80 | 75 | 28 |
| Isoph:SA (50:50) | 50 | 65 | 37 |
| | 50 | 48 | 36 |
| | 50 | 58 | 31 |

Prepolymers prepared by a reaction between a calculated amount of diacids and acetic anhydride for 30 min.
*Determined from 'H—NMR Spectrum The preceding examples demonstrate the usefulness of the pure, isolated prepolymers in the rapid preparation of a variety of polymer compositions as well as the high yield and reproducibility of the disclosed method.

High molecular weight polyanhydrides are desirable in biomedical applications, for exasmple, in controlled release devices because of their superior physiomechanical properties.

These properties include film forming properties and relatively high tensile strength. The critical factors affecting polymer molecular weight are: monomer purity, temperature of reaction, time of reaction, and the removal of the condensation product.

Very high molecular weight polymers are achieved by reacting pure isolated prepolymers, prepared in accordance with this invention, under optimized conditions, for example, at a temperature of 180° C., under $10^{-4}$ mm Hg vacuum with a $CO_2$/Acetone trap, as described in co-pending application U.S. Ser. No. 892,809 filed August 1, 1986 by Abraham J. Domb and Robert S. Langer entitled "Synthesis and Application of High Molecular Weight Polyanhydrides".

Using the prior art method, with an unisolated prepolymer mixture, p(CPP:SA)(1:4) has a molecular weight of 12,030. Reacting pure, individually prepared prepolymers yields p(CPP:SA)(1:4) with a molecular weight of 116,800 and an intrinsic viscosity of $[n]=0.92$. Addition of a catalyst to the pure, individually prepared prepolymer mixture can further increase molecular weights, as described in U.S. Ser. No. 892,809 filed Aug. 1, 1986.

The method of preparing very pure anhydride copolymers from individually synthesized and purified diacid prepolymers has been described with reference to specific embodiments. Variations and modifications of these embodiments and preparation conditions will be obvious to those skilled in the art of chemical synthesis. Such modifications and variations are intended to be included within the scope of the appended claims.

We claim:

1. A method for preparing highly pure anhydride copolymers comprising:
   providing at least two individually synthetized and purified diacids,
   reacting the individual diacids and acetic anhydride separately to form mixed anhydrides of the invididual diacids,
   separately removing the unreacted acetic anhydride and diacids from the individual mixed anhydrides formed by the reaction of the acetic anhydride with said diacids,
   combining said individual mixed anhydrides, and
   polymerizing said mixture of the purified mixed anhydrides of the individual diacids to form copolymers.

2. The method of claim 1 wherein the diacids are selected form the group consisting of sebacic acid, bis(p-carboxyphenoxy-propane, bis(p-carboxyphenoxy)hexane, isophthalic acid, 1,4 phenylene diporpionic acid, adipic acid and dodecanedioic acid.

3. A highly pure anhydride copolymer consisting essentially of individually synthetisized and purified monomers selected from the group consisting of mixed anhydrides of aliphatic and aromatic diacids, wherein said diacids were individually reacted with acetic anhydride and the unreacted diacid and acetic anhydride removed after the reaction.

4. The anhydride copolymer of claim 3 wherein said mixed anhydrides are formed by
   separately refluxing individual diacids with acetic anhydride to form individual mixed anhydrides,
   removing the excess acetic anhydride, and
   recrystallizing the individual mixed anhydrides.

5. The anhydride copolymer of claim 3 wherein the copolymers are further purified by recrystallization.

* * * * *

UNITED STATES PATENT AND TRADEMARK OFFICE
CERTIFICATE OF CORRECTION

PATENT NO. : 4,789,724                                Page 1 of 2

DATED : December 6, 1988

INVENTOR(S) : Abraham J. Domb et al.

It is certified that error appears in the above-identified patent and that said Letters Patent is hereby corrected as shown below:

Column 2, line 53, delete "ananhydride" and insert --a anhydride--.

Column 3, line 11 of Table 2, delete "CPH SA" and insert --CPH:SA--.

Column 3, line 54, delete "dodecannedioic" and insert --dodecanedioic--.

Column 3, line 59, delete "Bis(p-carobxyphenoxy)" and insert -- Bis(p-carboxyphenoxy--.

Column 3, lines 60 and 61, delete "Marcomol." and insert -- Macromol.--.

Column 6, line 64, delete "180 + 1°C" and insert --180 ±1°C--.

Column 7, line 36, delete "bis(p-carhoxyphenoxy)" and insert --bis(p-carboxyphenoxy).

Column 9, line 56, delete "exasmple" and insert --example--.

Column 9, line 57, delete "physio" and insert --physico--.

UNITED STATES PATENT AND TRADEMARK OFFICE
CERTIFICATE OF CORRECTION

PATENT NO. : 4,789,724

DATED : December 6, 1988

INVENTOR(S) : Abraham J. Domb et al.

It is certified that error appears in the above-identified patent and that said Letters Patent is hereby corrected as shown below:

> Column 10, line 45, delete "bis(p-carboxyphenoxy-propane," and insert --bis(p-carboxyphenoxy) propane,--.
>
> Column 10, line 49, delete "synthetisized" and insert --synthesized--.

Signed and Sealed this

Third Day of October, 1989

*Attest:*

DONALD J. QUIGG

*Attesting Officer*       *Commissioner of Patents and Trademarks*

UNITED STATES PATENT AND TRADEMARK OFFICE
CERTIFICATE OF CORRECTION

PATENT NO.    : 4,789,724
DATED         : December 6, 1988
INVENTOR(S)   : Abraham J. Domb and Robert S. Langer It is certified that error appears in the above-identified patent and that said Letters Patent is hereby corrected as shown below:

<u>Title page,</u>
The disclaimer notice should read as follows:
-- [*] Notice: This patent is subject to a disclaimer. --

Signed and Sealed this

Twenty-ninth Day of April, 2003

JAMES E. ROGAN
*Director of the United States Patent and Trademark Office*